United States Patent
Aman et al.

(10) Patent No.: US 10,624,651 B2
(45) Date of Patent: Apr. 21, 2020

(54) LIMITED USE TOOL REMOVABLE ATTACHMENT COMPONENTS

(71) Applicants: Peter M Aman, Austin, TX (US); Richard Acevedo, Austin, TX (US)

(72) Inventors: Peter M Aman, Austin, TX (US); Richard Acevedo, Austin, TX (US)

(73) Assignee: INSURGICAL, INC., Austin, TX (US)

( * ) Notice: Subject to any disclaimer, the term of this patent is extended or adjusted under 35 U.S.C. 154(b) by 690 days.

(21) Appl. No.: 15/090,612

(22) Filed: Apr. 4, 2016

(65) Prior Publication Data

US 2016/0345984 A1 Dec. 1, 2016

Related U.S. Application Data (60) Provisional application No. 62/168,834, filed on May 31, 2015.

(51) Int. Cl.
*A61B 17/00* (2006.01)
*A61B 17/16* (2006.01)
*A61B 17/14* (2006.01)

(52) U.S. Cl.
CPC ........ *A61B 17/1622* (2013.01); *A61B 17/142* (2016.11); *A61B 17/144* (2016.11); *A61B 17/162* (2013.01); *A61B 17/1626* (2013.01); *A61B 17/1624* (2013.01); *A61B 2017/00393* (2013.01); *A61B 2017/00734* (2013.01)

(58) Field of Classification Search
None
See application file for complete search history.

(56) References Cited

U.S. PATENT DOCUMENTS

| | | |
|---|---|---|
| 5,868,750 A | 2/1999 | Schultz |
| 2004/0249389 A1 | 12/2004 | Kim |
| 2009/0093830 A1* | 4/2009 | Miller ............. A61B 10/025 606/167 |
| 2009/0194446 A1 | 8/2009 | Miller |
| 2009/0326540 A1 | 12/2009 | Estes |
| 2012/0209317 A1 | 8/2012 | Oepen |
| 2014/0102742 A1* | 4/2014 | Eshleman ......... B25B 21/004 173/183 |

FOREIGN PATENT DOCUMENTS

| | | |
|---|---|---|
| EP | 1882538 A2 | 1/2008 |
| WO | 2014144757 A1 | 9/2014 |

* cited by examiner

*Primary Examiner* — Sameh R Boles
(74) *Attorney, Agent, or Firm* — ClearPat Services, LLC (57) ABSTRACT

A reusable medical procedure power too includes a housing having an aperture. A removable attachment interface is connected to the power tool via the aperture. The attachment interface provides for receiving a power tool attachment. A removable and replaceable cover is provided on the entire housing, and the cover includes a single opening aligned with and immediately adjacent to the aperture.

35 Claims, 12 Drawing Sheets

LIMITED USE TOOL REMOVABLE ATTACHMENT COMPONENTS

CROSS REFERENCE TO RELATED APPLICATION

The present application is related to and claims priority to U.S. Provisional Application No. 62/168,834 filed on May 31, 2015.

BACKGROUND

This disclosure relates generally to single use or limited use power tools and more particularly to external components that can be removed for cleaning when a tool is being cleaned, reconditioned, sterilized and deployed for re-use.

Important factors for any surgical instrument include sterility, cost of acquisition, maintenance, and reliability during use in the surgical suite. Each of these factors can have a significant impact on the cost of medical care for both the patient and the provider.

In recent years, there has been significant focus on the ever increasing cost of medical care. These cost increases have led to skyrocketing insurance premiums, reduced coverage, reduced reimbursements, increased fees for services, severe reductions in the services for some patient groups by some providers, and unfortunately an apparent increase in infections and medical mishaps.

In an effort to reduce costs and improve profitability, both service providers and medical device suppliers are continuously looking for ways to streamline procedures, reduce time, cost, and risk from their products and services without reducing the quality of the products or services they provide to their customers. One area to benefit from these savings and improvements has been in the orthopedic surgical field through the use of high precision, battery powered surgical instrumentation. In the late 1960's and early 1970's battery operated drills were bulky, ill-balanced and required multiple batteries to perform some surgeries due to the limited energy storage capacity and poor efficiency of the electric motors.

Since then, manufacturers have attempted to make batteries more efficient with higher energy storage capacity, reduced size, and improved rechargeable lifespans. Likewise, motor housings such as saw and drill bodies have become more ergonomic, balanced, lightweight and energy efficient. As with many standard hand tools having multiple moving components, instrument manufacturers have reduced weight by utilizing lighter materials such as plastic housings, and gears, and put weight reducing apertures in what were previously solid housings. In some cases, standard mountings for attachments have been replaced with modular fittings, allowing for greater interchangeability and component selections. Additionally, manufacturers have attempted to improve electrical components by upgrading them with more modern components wherever possible.

All of these improvements in equipment have improved efficiencies, costs and quality in some areas while at the same time increasing costs for acquisition, maintenance and increasing patient risks in other ways that were not previously seen or predicted. Often times cost, quality and risk can be inversely proportional to one another. One example of the increased cost and reduced patient risk is seen in the cleaning and maintenance of instruments.

Recent published reports suggest that many of the surgical instruments used in operations were not being cleaned and/or sterilized appropriately in the very hospital facilities that were established and tasked for that purpose. In numerous reports, following cleaning and sterilization, it was noted that upon closer secondary inspection, the inside of small diameter cannulas and intricate mini-components of arthroscopic shavers that are used for many of today's minimally invasive procedures, contained human tissue and bone fragments from previous surgeries. In other cases, modular components of drills and saws such as chucks, drill bits and blades were found to have similar debris or pieces of cleaning brushes and/or bristles embedded in or on them. These investigations have demonstrated that in most cases the instruments were not cleaned according to manufacturer's specifications which has likely led to many documented cases of serious, multiple, serial infections for subsequent patients. A pilot program conducted by the Centers for Medicare and Medicaid Services (Schaefer et al., 2010; JAMA 2010; 303(22):2273-2279) inspected 1500 outpatient surgery centers and found that 28% had been cited for infectious control deficiencies associated with equipment cleaning and sterilization. The costs to the patients and the hospitals in both expense and liability to deal with these infections can be and has been staggering.

In other cases, critical battery-operated, motorized tools such as drills or bone saws have ceased to function due to dead batteries that no longer maintain their capacity to hold a charge, or due to internal part failure, often attributable to overuse or lack of proper maintenance. The resultant downtime in the operating suite is extremely costly, as the procedure step must be put on hold while replacement or substitute tools are obtained. Wait times may often exceed 20-30 minutes, resulting in additional anesthesia exposure for the patient, additional operating room time (charged to the patient) and potential delays to other procedures where the replacement or substitute equipment had been scheduled for use in a later procedure. Recent estimates (2005) establish the average cost of operating room time to range between $62/min. (range $21.80-$133.12) depending on the procedure. These figures did not include extra resources provided by the hospital for special, non-routine situations which often occur during standard procedures, and did not include the surgeon and anesthesia provider fees, (anesthesia fees are estimated to be $4/min; range $2.20-$6.10).

Hospitals and instrument manufacturers are continuously attempting to find improved ways to reduce risk associated with infection in general, and more recently, specifically from improperly cleaned instruments. One approach has been to use more disposable, single-use instruments such as drills, saw blades and plastic cannulas. Additionally, many laparoscopic devices, such as surgical staplers and trocars, are designed as single use items that are intended to be immediately disposed of after use. Unfortunately, at today's acquisition costs, the total cost of ownership and benefits are not always clear for high-use battery-operated, motorized instruments such as saws, drills and reamers used in orthopedic procedures and the idea of disposable powered instruments has not been readily embraced.

A recent trend in the medical community is the reprocessing of single use medical instruments, by parties other than the original equipment manufacturer, instead of discarding them after use. During reprocessing, the medical instruments are disassembled, cleaned and sterilized. They are then reassembled for future use. However, because the medical instruments reprocessed for further use are specifically provided for use during a single procedure, the performance of the medical instruments tends to decline after reprocessing, because the components making up the medical instrument are not adapted for multiple uses and will degrade in performance when used beyond their intended life span. For example, reprocessing of the cutting devices on trocars is intended to extend these devices beyond their intended mission life, but often results in duller cutting edges on the blades because neither the materials used nor the reprocessing method can restore the device to the original manufacturing specifications. A greater force, therefore, is needed to make an initial incision, causing more trauma to the patient. In addition, the use of greater force increases the potential for error during the surgical procedure.

Most hospitals and surgery centers buy high-use, reusable motorized, pneumatic, wired or battery operated, orthopedic surgical equipment and are expected to clean, sterilize, and maintain them internally within the hospital. Unfortunately, the technicians hired to perform this work are typically not qualified or trained to perform this work adequately for the many varieties of powered instruments used. Further, manufacturers rarely provide the hospital/client with the training or diagnostic equipment necessary to evaluate or test the equipment. Often times the hospital employees responsible for cleaning and maintenance are not technicians at all, being paid slightly more than minimum wage, working at a fast pace to merely wash, count, and reload instruments into their appropriate system trays and flash sterilize them as quickly as possible, in an effort to keep the equipment in rotation in the hospital operating rooms, where higher throughput dictates profitability for the hospital or surgery center.

As a result of high throughput requirements, general maintenance is rarely done and preventative monitoring and maintenance is almost never done on this type of equipment. Hospital budgets for internal maintenance of equipment are generally geared toward high-end, multi-million dollar capital equipment such as x-ray and radiological equipment. It is generally assumed that it is faster, simpler, and more economical for the hospital to wait for hand-held instruments, such as drills, saws and reamers to fail, then, send them back to the manufacturer for repair or replacement. Thus it has become apparent that there is a need for an improved system of cost-effective, battery-operated, motorized tools in conjunction with better cleaning and maintenance protocols which can provide the hospital, surgeon, and most importantly, the patient, with a higher degree of efficiency and cleanliness while reducing risk and keeping the costs of cleaning, maintenance, and repair as low as possible.

SUMMARY

Accordingly, in one embodiment, a reusable medical procedure power tool includes a housing an aperture. A removable attachment interface is connected to the power tool via the aperture, the attachment interface including means for receiving a power tool attachment. A removable and replaceable cover is provided on the entire housing, and the cover includes a single opening aligned with and immediately adjacent to the aperture.

DETAILED DESCRIPTION

Figure 1:
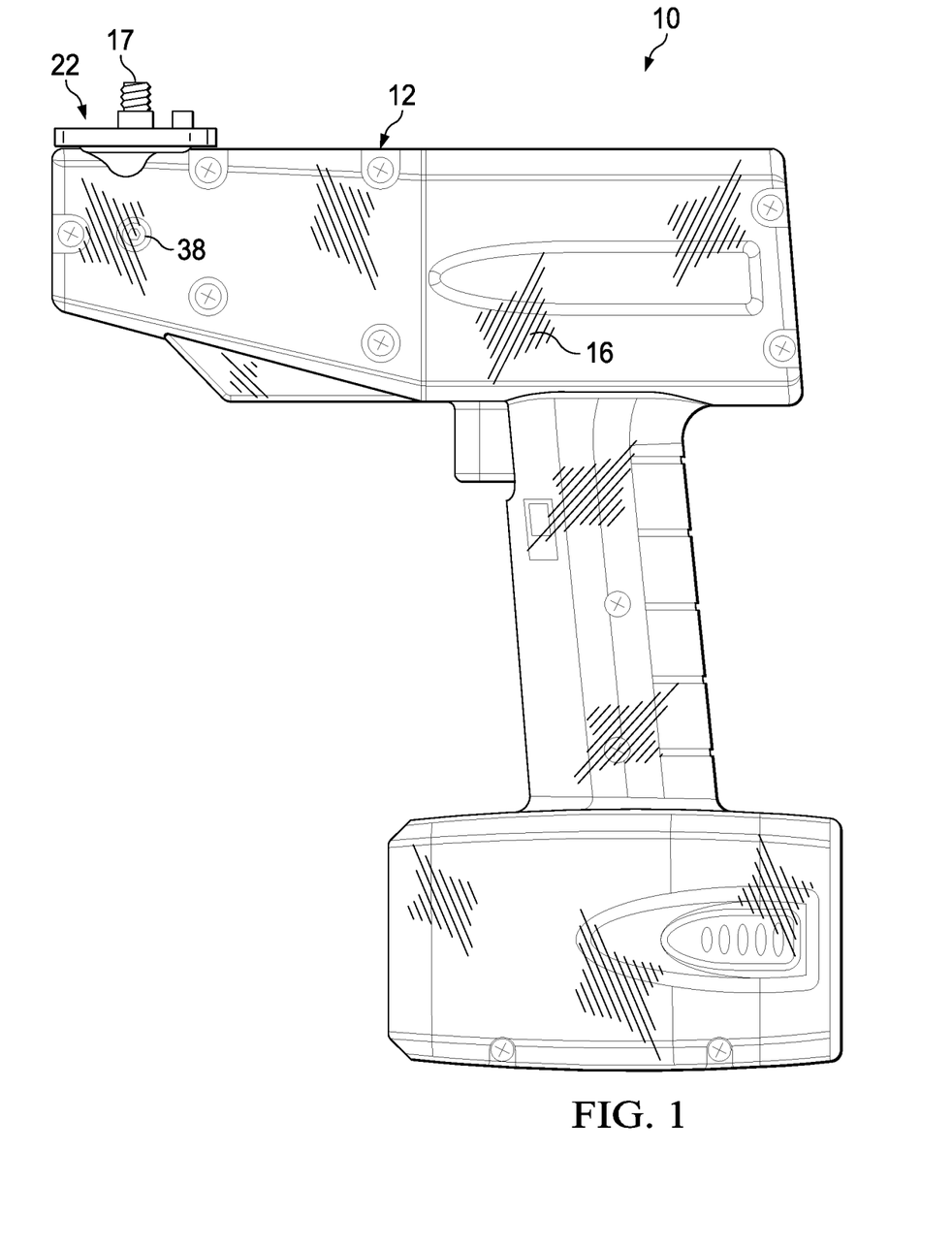
FIG. 1 is a view illustrating an embodiment of a reusable medical procedure power tool.
Figure 2:
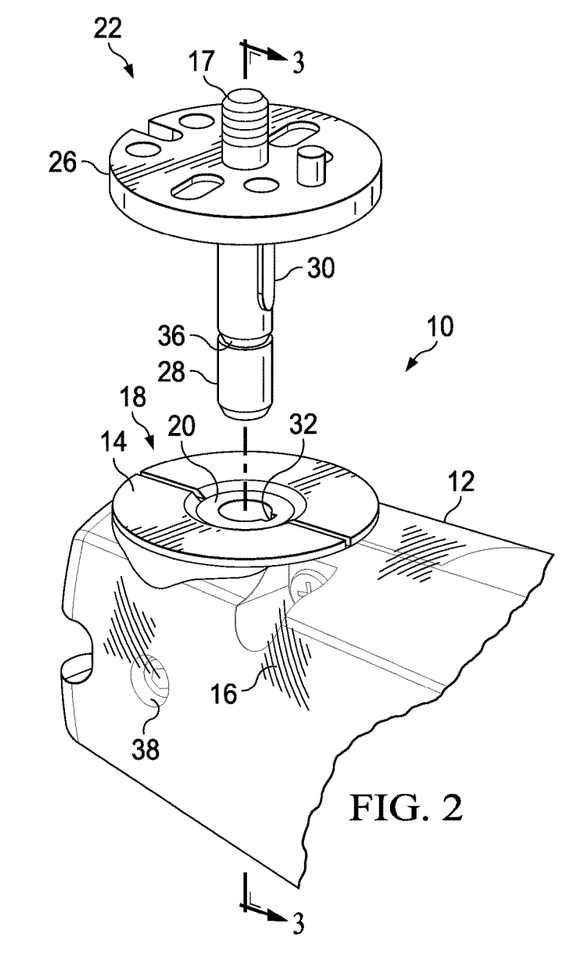
FIG. 2 is a partial perspective view illustrating an embodiment of an attachment interface removed from the power tool of FIG. 1.
Figure 3:
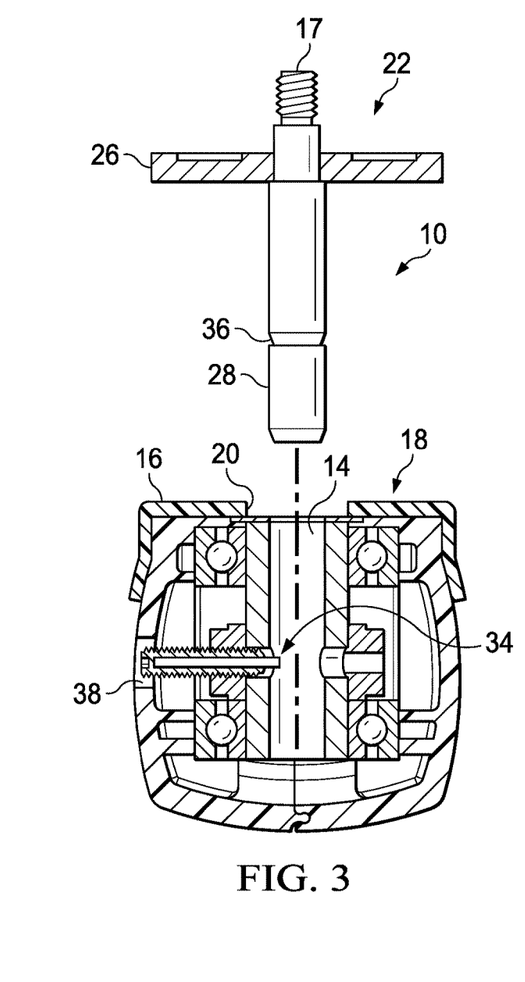
FIG. 3 is a cross-sectional view taken along the line 3-3 of FIG. 2.

In FIG. 1, a reusable medical procedure power tool 10 includes a housing 12 and an aperture 14, see also FIG. 2. A removable and replaceable cover 16, of a sealing, synthetic material, FIG. 1, covers the entire housing 12 including an attachment base 18, FIG. 2. Cover 16, partially shown in FIG. 3, includes a single opening 20, which is concentrically aligned with the aperture 14, FIGS. 2 and 3. A removable attachment interface 22, FIGS. 2 and 3, is connected to the power tool 10 via the aperture 14 in the attachment base 18. The removable attachment interface 22, including a threaded stud 17, can receive an oscillating saw blade, discussed below. The attachment interface 22 in this embodiment FIGS. 2 and 3, includes a pivot shaft assembly having a base 26, a shaft 28 and a key 30 on the shaft 28. A keyway 32 in the aperture 14 receives the key 30.

After use of tool 10, FIG. 3 attachment interface 22 can be removed from aperture 14 by release of a retaining pin 34 which retains shaft 28 by engagement with a groove 36. An access opening 38, FIG. 2, quick-releases pin 34 from groove 36. Once attachment interface 22 is removed, it can be cleaned separately from tool 10. The tool 10 cover 16 is removed and only the aperture 14 and adjacent areas of tool 10, FIG. 3, require cleaning. The tool 10 may then be recovered with a replacement cover 16, and attachment interface 22 may be re-inserted in aperture 14. The entire re-assembled tool is then sterilized and is ready for future use.

Figure 4:
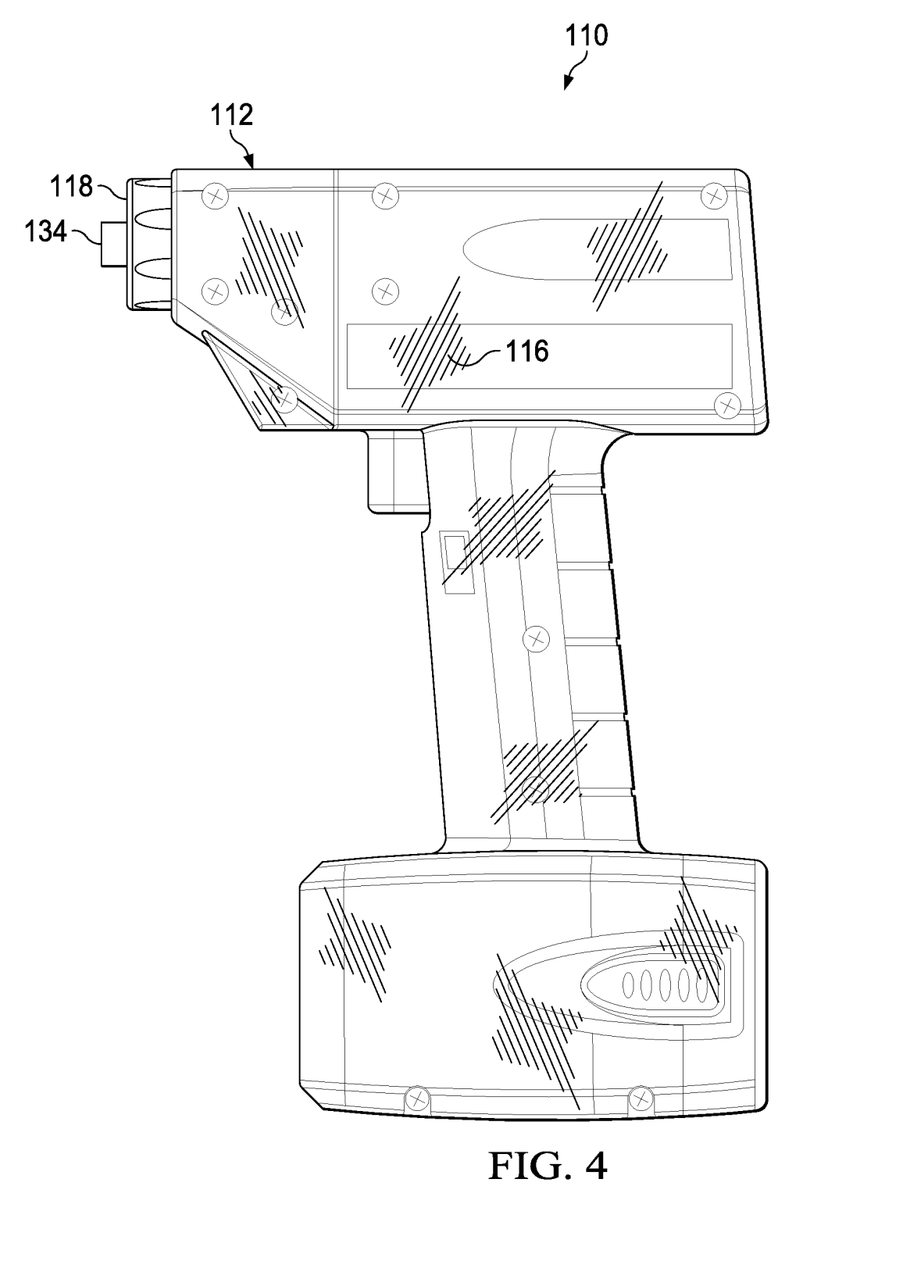
FIG. 4 is a side view illustrating an embodiment of a reusable medical procedure power tool.
Figure 5:
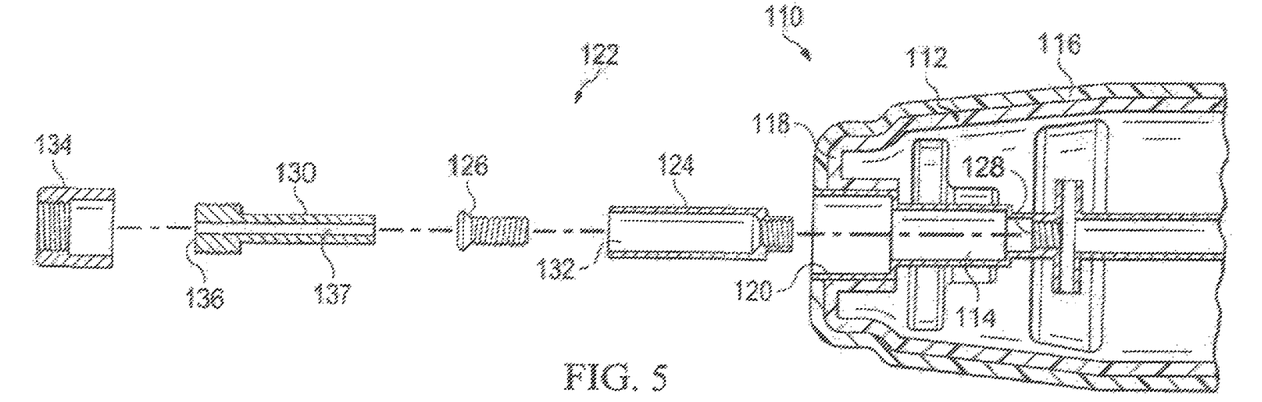
FIG. 5 is a partial cross-sectional side view illustrating an embodiment of an attachment interface removed from the power tool of FIG. 4.
Figure 6:
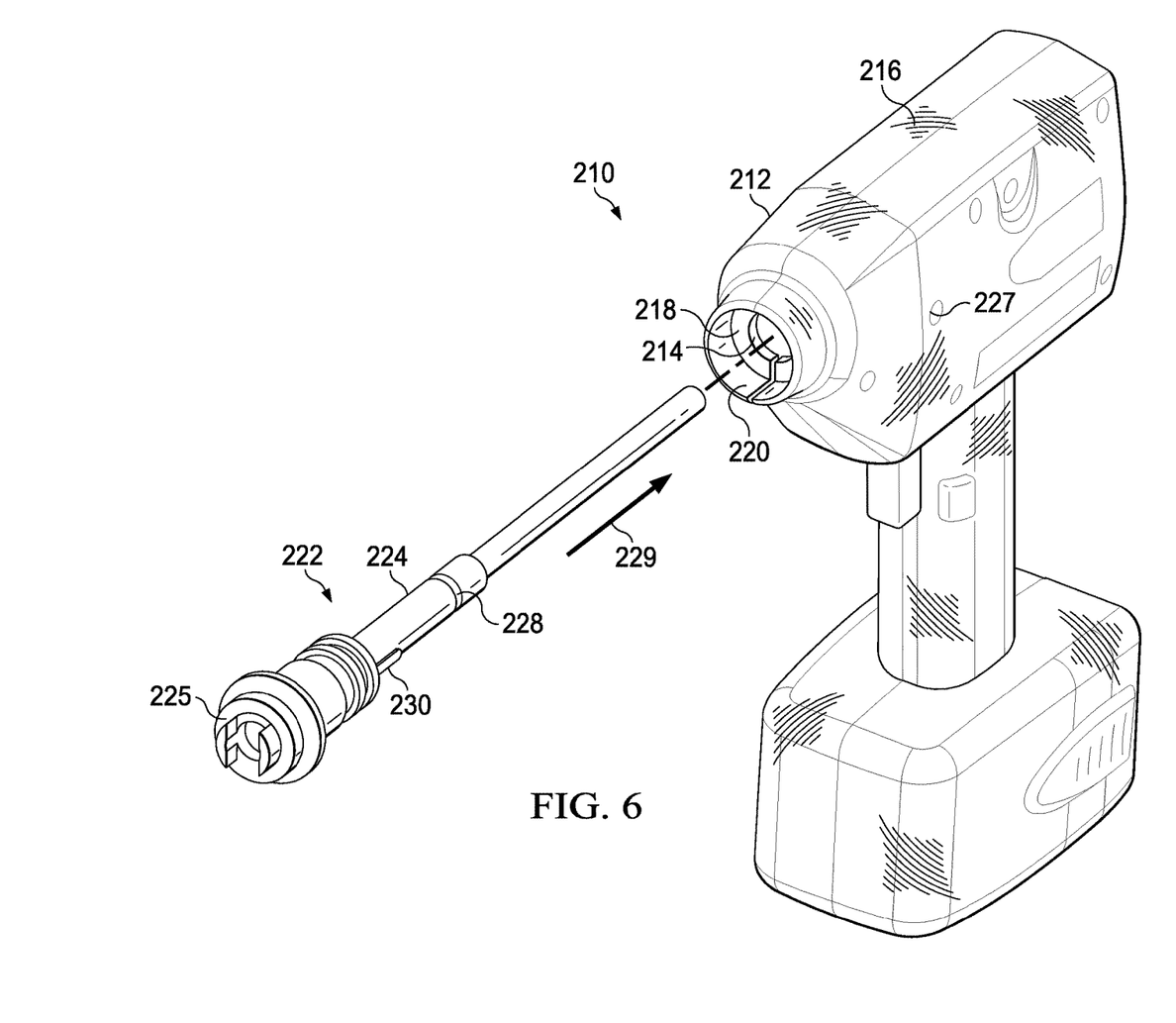
FIG. 6 is a perspective view illustrating an embodiment of a reusable medical procedure power tool and an insertable output shaft assembly.
Figure 7:
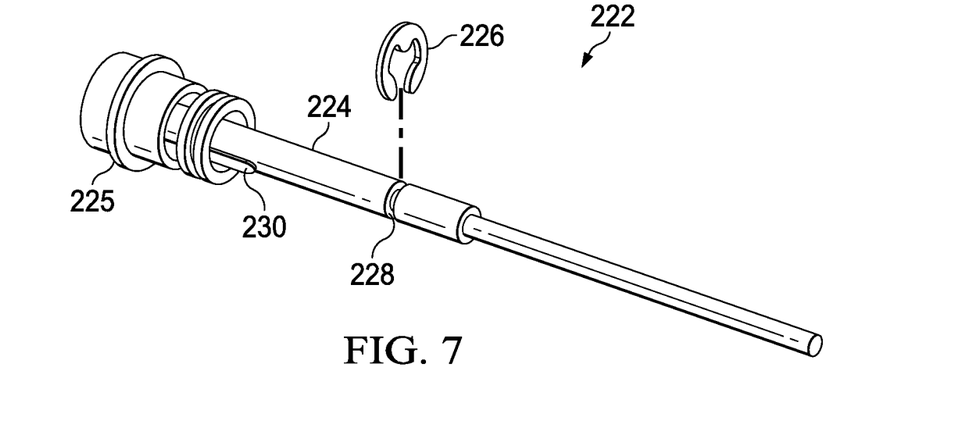
FIG. 7 is a perspective view illustrating an embodiment of the output shaft assembly detached from the power tool of FIG. 6.

In FIGS. 4 and 5, a reusable medical device power tool 110 includes a housing 112 and an aperture 114. A removable and replaceable cover 116, as described above, covers the entire housing 112 including an attachment base 118. Cover 116, partially shown in FIG. 5, includes a single opening 120, which is concentrically aligned with the aperture 114. A removable attachment interface 122 is connected to the power tool 110 via the aperture 114 in the base 118. The removable attachment interface 122 can receive a reciprocating saw blade, discussed below. The attachment interface 122 in this embodiment includes a collet shaft 124 retained in the tool 110 by a locking screw 126 received at threads 128. A blade jaw retainer 130 inserts into aperture 132 of collet shaft 124 and can receive a reciprocating saw blade in a slot 137. A collet nut 134 is threaded on an end 136 of blade jaw retainer 130.

After use of the tool 110, attachment interface 122 can be removed from aperture 114 by release of collet nut 134 and locking screw 126. Once attachment interface 122 is removed, it can be cleaned separately from tool 110. The cover 116 is removed and only the aperture 114 and adjacent areas of tool 110 require cleaning. The tool 110 may then be recovered with a replacement cover 116, and attachment interface 122 may be re-inserted in aperture 114. The entire re-assembled tool is then sterilized and is ready for future use.

In FIGS. 6, 7, 8 and 9, a reusable medical device power tool 210 includes a housing 212 and an aperture 214. A removable and replaceable cover 216, as described above, covers the entire housing 212 including an attachment base 218. Cover 216 includes a single opening 220, which is concentrically aligned with the aperture 214. A removable output shaft attachment interface 222 is connected to the power tool 210 via the aperture 214 in the base 218. The output shaft interface 222 can include, for example, a Zimmer-Hall rotational connector 225 for receiving rotational tools, discussed below, such as drilling or reaming tools. The output shaft interface 222 in this embodiment includes an output shaft 224 which is inserted to extend into tool 210 in a direction of arrow 229, so as to be secured in the tool 210 by a "C" clip 226 snapped into a groove 228 on shaft 224. The shaft 224 includes a key 230 which synchronizes rotation of shaft 224 with the driving mechanism within the tool 210 due to engagement with a keyway (not shown) in the tool 210.

Figure 8:
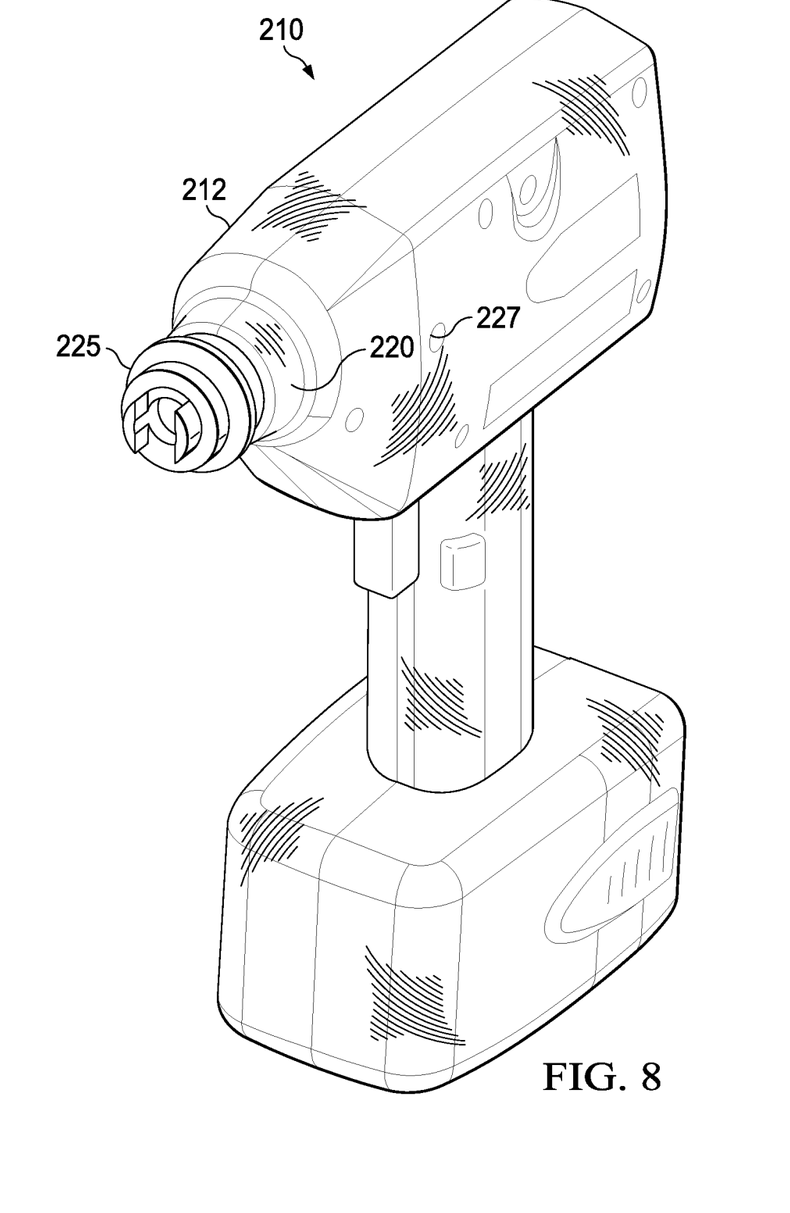
FIG. 8 is a perspective view illustrating the power tool of FIG. 6, having the output shaft assembly inserted into the power tool.
Figure 9:
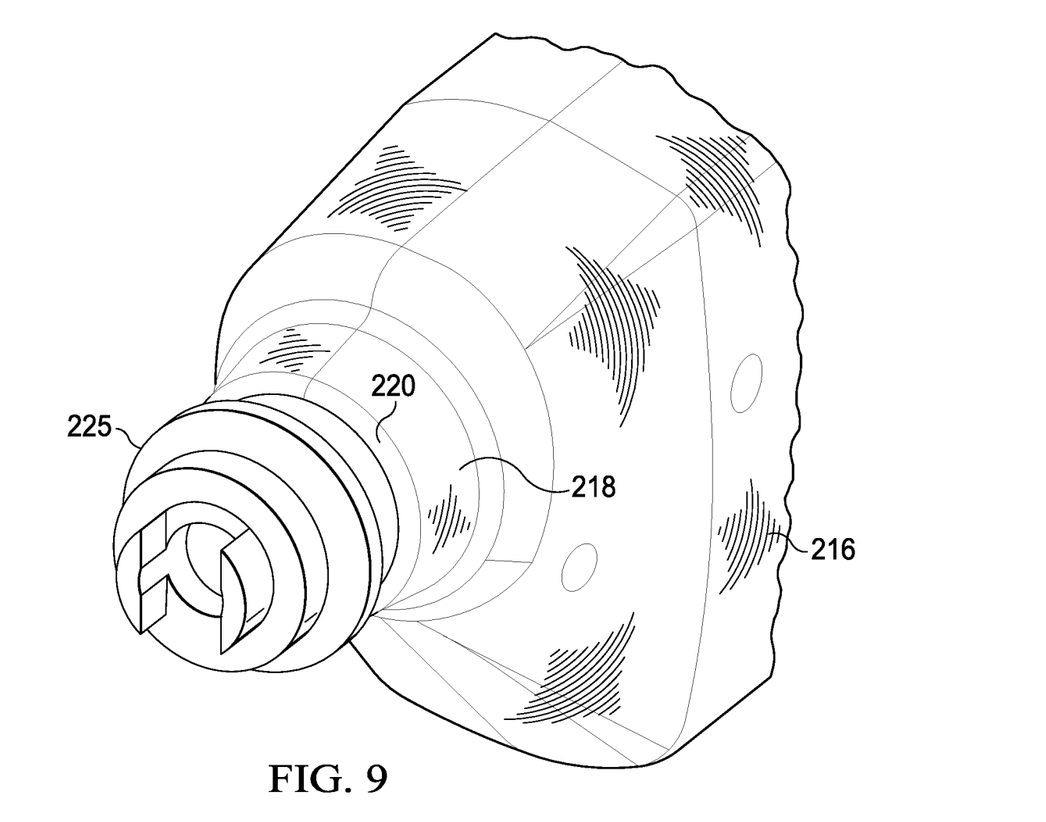
FIG. 9 is a partial perspective view illustrating a rotational member for receiving a drilling/reaming tool.

When fully inserted, FIGS. 8 and 9, shaft 224 extends into housing 212 so that rotational connector 225 seats in aperture 214. After use of tool 210, interface 222 is removed by means of removing "C" clip 226 via an access hole 227. The interface 222 can then be cleaned separately from tool 210. The cover 216 is removed and only the aperture 214 and immediately adjacent areas of tool 210 require cleaning. The tool 210 may then be recovered with a replacement cover 216, and interface 222 may be re-inserted in aperture 214. The entire re-assembled tool is then sterilized and is ready for future use. The cover 216 has tight fitting opening 220 to attachment interface 218.

Figure 10:
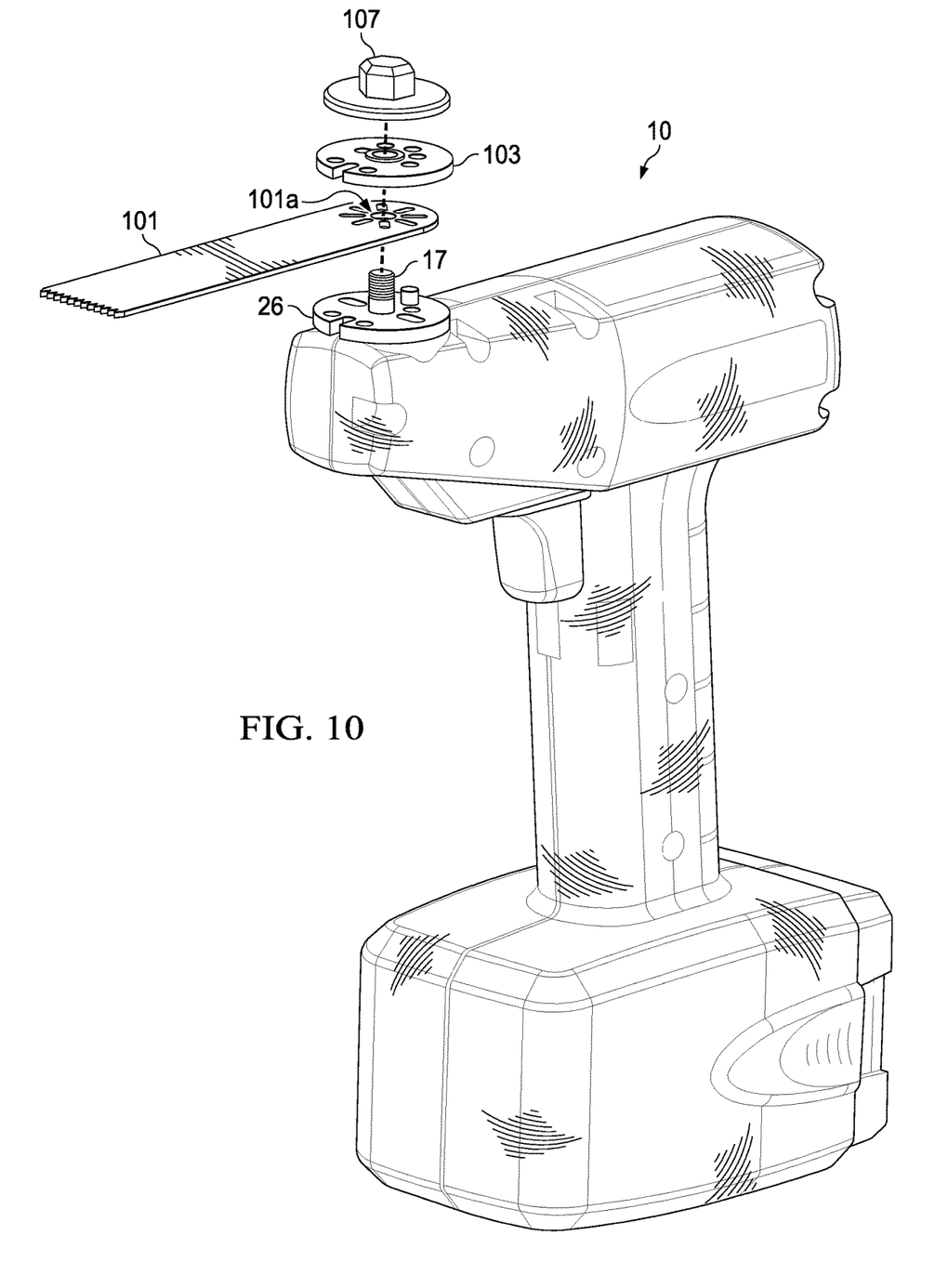
FIG. 10 is an exploded perspective view illustrating the power tool of FIGS. 1-3 utilizing an oscillating power tool attachment interface.
Figure 11:
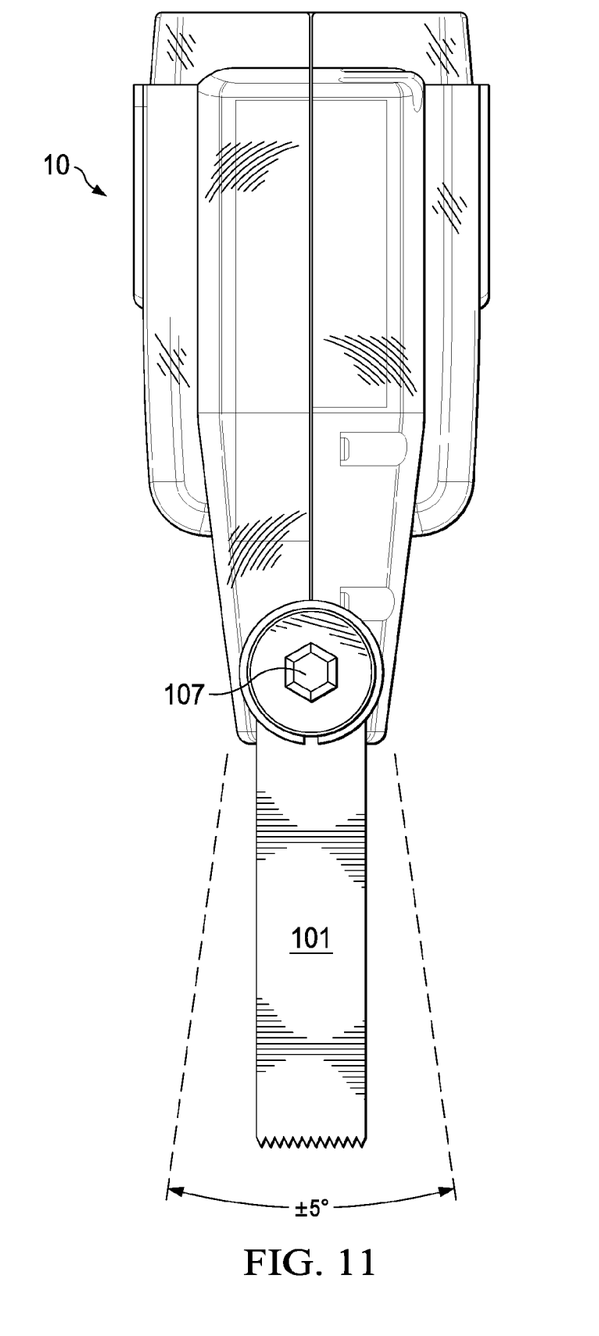
FIG. 11 is a top view of the power tool of FIG. 10 illustrating an approximate range of oscillation of the power tool attachment.

In operation, the medical procedure power tool 10, FIGS. 1-3, is further disclosed in FIGS. 10 and 11. An oscillating saw blade 101 is received via an aperture 101a on threaded stud 17 and retained on the stud 17 between base 26 and a plate 103. A washer/nut assembly 107 seats on plate 103 and is threaded onto stud 17. The blade 101 has a range of oscillation of approximately 5°. Alternately, other connection schemes may be used to connect the interface 22 to an attachment, such as for example, a quick-connect, quick disconnect saw blade device.

Figure 12:
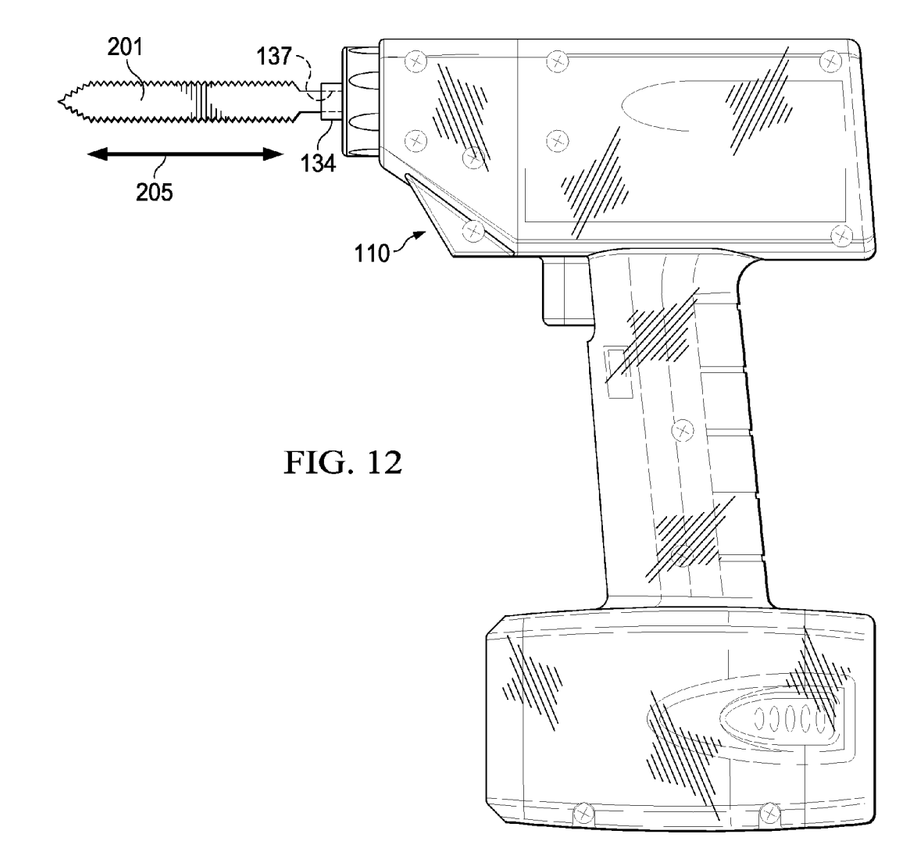
FIG. 12 is a side view illustrating the power tool of FIGS. 4 and 5 utilizing a reciprocating power tool attachment.

The medical procedure power tool 110, FIGS. 4 and 5 is further disclosed in FIG. 12. A reciprocating saw blade 201 is received in the slot 137. The collet nut 134 clamps the saw blade 201 in the slot 137. The blade 201 reciprocates along a path illustrated by the bi-directional arrow designated 205.

Figure 13:
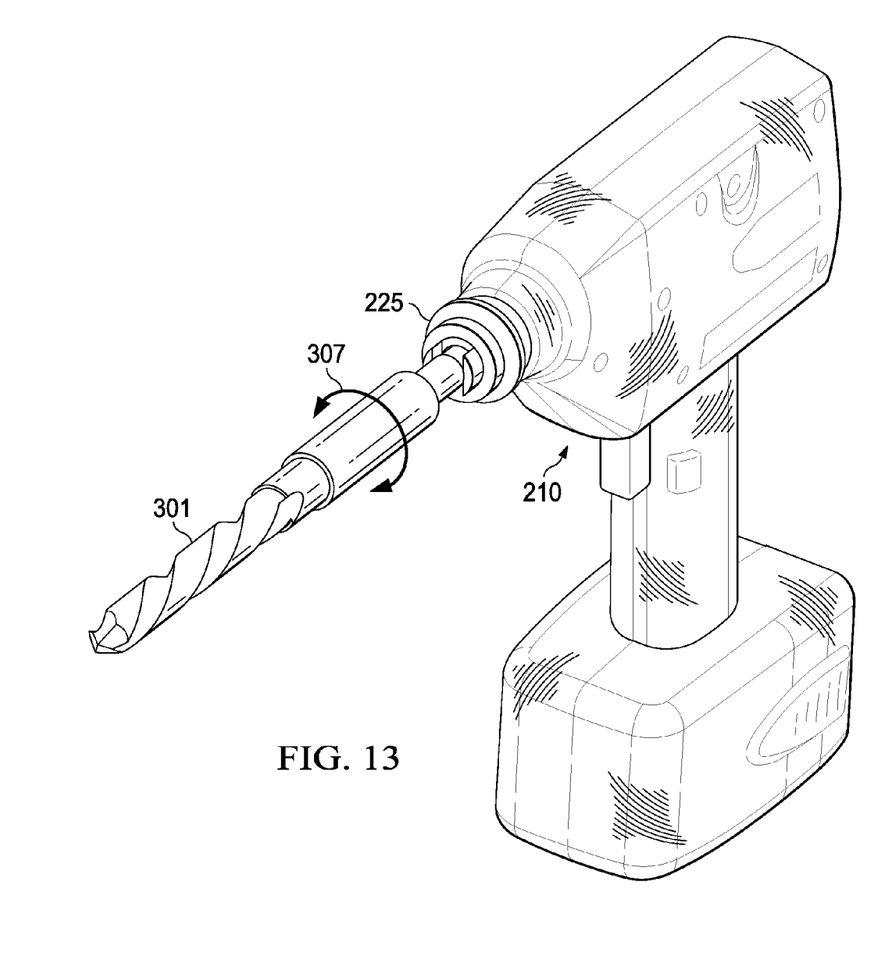
FIG. 13 is a perspective view illustrating the power tool of FIGS. 6-9 utilizing a rotary drilling attachment.
Figure 14:
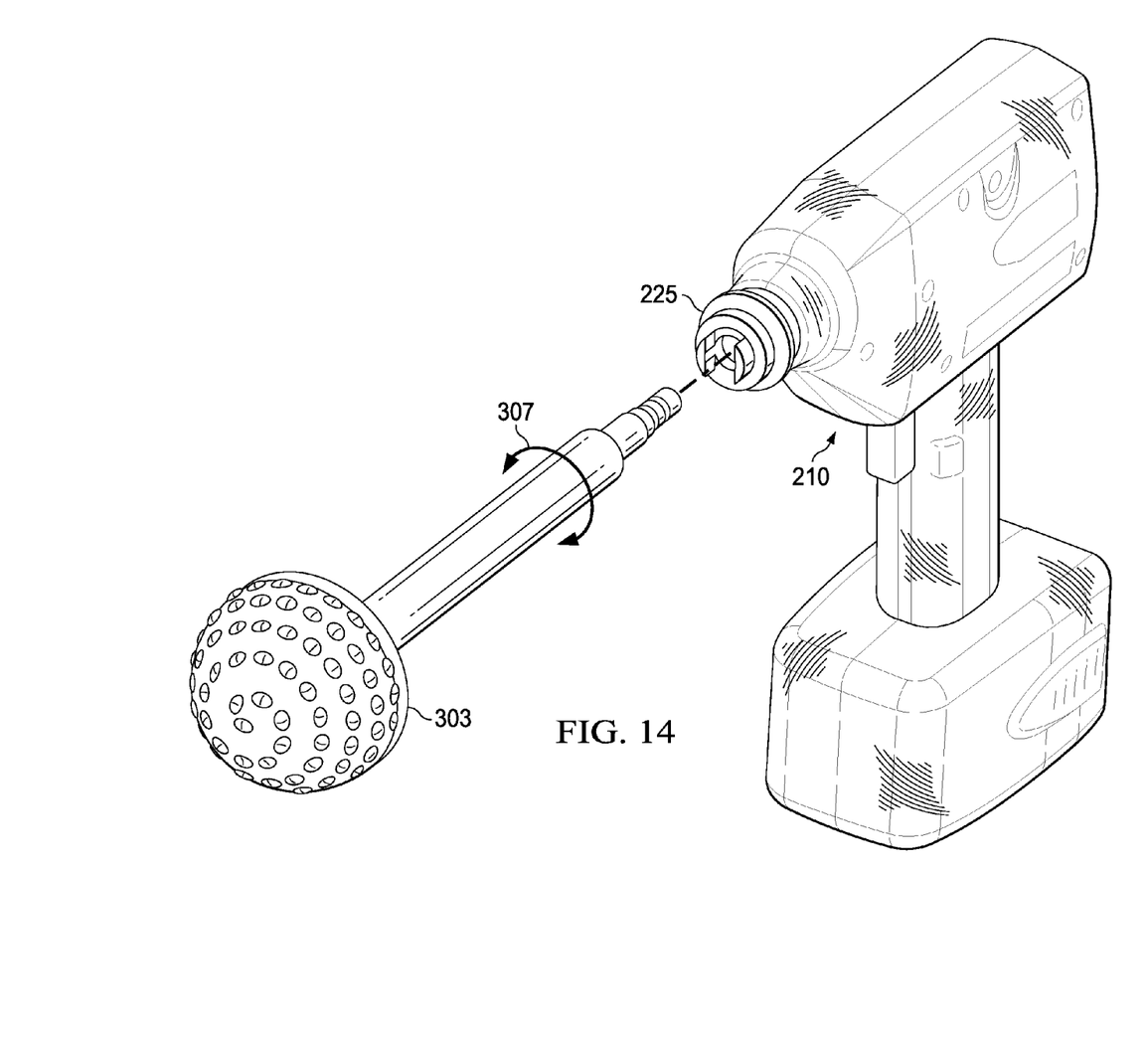
FIG. 14 is a perspective view illustrating the power tool of FIG. 13 utilizing a rotary reaming attachment.

The medical procedure power tool 210, FIGS. 6-9, is further disclosed in FIGS. 13 and 14. A rotary drill bit 301 or, alternatively, a rotary reamer 303 is received via the connector 225. The rotary motion of both the drill bit 301 and the reamer 303 is illustrated by the arcuate bidirectional arrow designated 307.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A pre-sterilized reusable medical procedure power tool comprising:
   a housing including an attachment receiving aperture;
   a removable attachment interface connected to the power tool via a shaft inserted into the aperture, the removable attachment interface including features for receiving a power tool attachment; and
   a closely conforming removable and replaceable cover comprising a sealing, synthetic material over the entire housing, the cover including a single opening concentrically aligned with the attachment receiving aperture, and immediately adjacent to the aperture.

2. The power tool of claim 1, wherein the power tool attachment is an oscillating tool.

3. The power tool of claim 1, wherein the aperture includes at least one recessed drive surface.

4. The power tool of claim 3,
   wherein the shaft of the removable attachment interface comprises at least one raised drive surface (key) configured to mate with the recessed drive surface (keyway) of the aperture and an annular groove.

5. The power tool of claim 4, wherein the housing includes an access opening and a quick release pin mounted in the access opening.

6. The power tool of claim 4, wherein, in response to the shaft being mounted in the aperture, the at least one raised drive surface (key) engages the at least one recessed drive surface.

7. The power tool of claim 4, further comprising:
   the attachment interface including a rotational tool connector mounted on the shaft, the rotational tool connector being seated in proximity to the housing so as to cover the aperture.

8. The power tool of claim 4, further comprising: a non-removable portion surrounding the aperture, forming an attachment base,
   wherein the closely conforming removable and replaceable cover further covers the attachment base and immediately adjacent to the aperture.

9. The power tool of claim 8, wherein the housing includes an access opening and a quick release pin mounted in the access opening.

10. The power tool of claim 8, wherein the removable attachment interface includes a pivot shaft assembly having a base for an oscillating tool.

11. The power tool of claim 1, wherein the power tool attachment is a reciprocating tool.

12. The power tool of claim 1, wherein the aperture includes a threaded receiver.

13. The power tool of claim 12, further comprising:
   the attachment interface including the rotational tool connector retained in the aperture by a threaded member;
   the rotational tool connector being seated in proximity to the housing adjacent the aperture.

14. The power tool of claim 13, wherein, the cap is seated adjacent the aperture.

15. The power tool of claim 13, wherein the rotational tool connector is configured to receive a drill or a reamer.

16. The power tool of claim 1, further comprising:
the attachment interface including a shaft having an annular groove, the shaft being received in the aperture.

17. The power tool of claim 16, wherein the housing includes an access opening and a "c" clip mounted in the annular groove, the access opening providing access to the "c" clip permitting removal of the attachment interface from the aperture.

18. The power tool of claim 17, further comprising:
the attachment interface including a rotational connector for receiving a rotational tool, the rotational connector being seated in proximity to the housing adjacent the aperture.

19. The power tool of claim 1, wherein the power tool is battery operated.

20. A pre-sterilized reusable medical procedure power tool comprising:
a housing including an aperture having an annular inner surface;
a closely conforming removable and replaceable cover comprising a sealing, synthetic material on the entire housing, the cover including a single opening concentrically aligned with and immediately adjacent to the aperture; and
a removable attachment interface connected to the power tool via a shaft inserted into the aperture, the removable attachment interface including capture features for receiving a power tool attachment connector, the capture features for receiving the power tool attachment connector having an annular outer surface aligned with and immediately adjacent the annular inner surface of the aperture when connected to the power tool.

21. The power tool of claim 20 wherein the power tool attachment is an oscillating tool.

22. The power tool of claim 20 wherein the power tool attachment is a reciprocating tool.

23. The power tool of claim 20 wherein the power tool attachment is a rotating tool comprising a drill or reamer.

24. The power tool of claim 20, wherein the power tool is battery operated.

25. The power tool of claim 20, wherein the aperture includes at least one recessed drive surface, (keyway) and,
wherein the shaft of the removable attachment interface comprises at least one raised drive surface (key) configured to mate with the recessed drive surface (keyway) of the aperture and an annular groove.

26. The power tool of claim 25, wherein the housing includes an access opening and a quick release pin mounted in the access opening.

27. The power tool of claim 26, further comprising:
the removable attachment interface including a rotational tool connector mounted on the shaft, the rotational tool connector being seated in proximity to the housing so as to cover the aperture.

28. The power tool of claim 26, further comprising: a non-removable portion surrounding
the aperture, forming an attachment base,
wherein the closely conforming removable and replaceable cover further covers the attachment base and immediately adjacent to the aperture, and
wherein the housing includes an access opening and a quick release pin mounted in the access opening.

29. The power tool of claim 28, wherein the removable attachment interface includes a pivot shaft assembly having a base for an oscillating tool.

30. A method for providing a reusable medical procedure power tool comprising:
providing a housing on the surgical power tool, the housing including an aperture having an annular inner surface;
covering the entire housing with a removable and replaceable cover, the cover including a single opening concentrically aligned with and immediately adjacent to the aperture; and
connecting a removable attachment interface to the power tool via the aperture, the attachment interface including means for receiving a power tool attachment, the means for receiving the power tool attachment having an annular outer surface immediately adjacent the annular inner surface of the aperture.

31. The method of claim 30, further comprising:
using the power tool for a medical procedure.

32. The method of claim 31, further comprising:
upon completion of the medical procedure, removing and cleaning the attachment interface.

33. The method of claim 32, further comprising:
cleaning the attachment receiving aperture and immediately adjacent housing surfaces.

34. The method of claim 33, further comprising:
removing the used cover and replacing a clean cover on the housing.

35. The method of claim 34, further comprising:
re-assembling the cleaned power tool including the attachment interface and the clean
cover; and utilizing the cleaned and re-assembled power tool.

* * * * *